United States Patent
De Coulon et al.

(10) Patent No.: US 9,140,659 B2
(45) Date of Patent: Sep. 22, 2015

(54) GAS SENSOR AND METHOD FOR DETERMINING A CONCENTRATION OF GAS IN A TWO-COMPONENT MIXTURE

(71) Applicant: BELENOS CLEAN POWER HOLDING AG, Bienne (CH)

(72) Inventors: Yves De Coulon, Wavre (CH); Vincent Demarne, Neuchatel (CH)

(73) Assignee: Belenos Clean Power Holding AG, Bienne (CH)

( * ) Notice: Subject to any disclaimer, the term of this patent is extended or adjusted under 35 U.S.C. 154(b) by 231 days.

(21) Appl. No.: 13/623,548

(22) Filed: Sep. 20, 2012

(65) Prior Publication Data

US 2013/0081445 A1    Apr. 4, 2013

(30) Foreign Application Priority Data

Sep. 29, 2011 (EP) .................................. 11183314
Apr. 4, 2012 (EP) .................................. 12163201

(51) Int. Cl.
*G01N 33/00* (2006.01)
*G01N 27/18* (2006.01)

(52) U.S. Cl.
CPC ............ *G01N 27/18* (2013.01); *G01N 33/0004* (2013.01)

(58) Field of Classification Search
CPC ................................................ G01N 33/0004
USPC ............................................ 73/25.01, 25.03
See application file for complete search history.

(56) References Cited

U.S. PATENT DOCUMENTS

2006/0254340 A1* 11/2006 Baraket et al. ................ 73/24.01
2009/0320561 A1* 12/2009 Fritz et al. ..................... 73/24.02
2010/0116024 A1* 5/2010 De Coulon et al. .......... 73/25.03
2010/0154510 A1 6/2010 Viens et al.

FOREIGN PATENT DOCUMENTS

| DE | 4228484 A1 | 3/1994 |
| EP | 2048759 A1 | 4/2009 |
| EP | 2381248 A1 | 10/2011 |
| GB | 1145751 A | 3/1969 |
| WO | 99/34201 A1 | 7/1999 |
| WO | 2008/053729 A1 | 5/2008 |
| WO | 2008/101822 A1 | 8/2008 |

OTHER PUBLICATIONS

European Search Report of EP 12 16 3201 dated Jul. 4, 2012.

\* cited by examiner

*Primary Examiner* — Laura Martin
*Assistant Examiner* — Alex Devito
(74) *Attorney, Agent, or Firm* — Sughrue Mion, PLLC

(57) ABSTRACT

The described sensor allows determination of the concentration of a gas in a two-component mixture at variable pressure by measuring the diffusivity and the thermal conductivity. The sensor is provided to alternately heat the membrane (12) of a thermally conductive cell (1) and allow it to cool such that the temperature $T_M$ of the membrane passes from a first stable value to a second stable value and vice versa via a transient mode. The cell produces a signal representative of the temperature $T_M$ of the membrane and the sensor extracts from the signal a first and a second parameter that respectively relate to said first stable value and said transient mode of the signal. A value of the concentration of said gas and of the pressure of said two-mixture is calculated from these two parameters.

6 Claims, 1 Drawing Sheet

Figure 1:
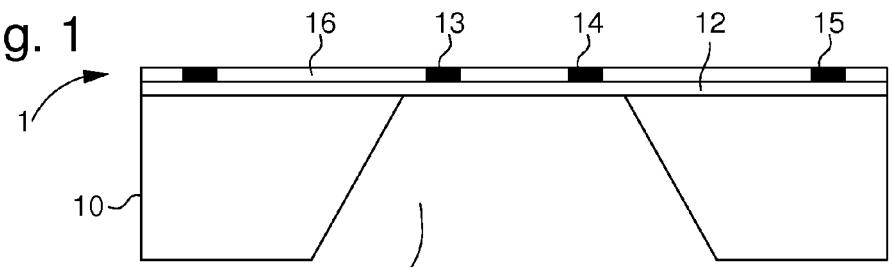

GAS SENSOR AND METHOD FOR DETERMINING A CONCENTRATION OF GAS IN A TWO-COMPONENT MIXTURE

The present invention relates to the field of thermal gas sensors. More specifically, it relates to a thermal gas sensor for determining a concentration of gas in a two-component mixture at variable pressure. It also relates to a method for determining a concentration of gas in a two-component mixture of variable concentration.

Thermal gas sensors take advantage of thermal conductivity properties of the gases to provide information on the nature of a gas or its concentration in a gaseous mixture. The thermal conductivity $\lambda$ of a gas is its capacity to transport heat under the effect of a temperature gradient. It is an intrinsic magnitude of a gas at a given pressure and temperature and this is why its measurement is able to provide an indication of the composition of a gaseous mixture. Thermal gas sensors are used in particular for measuring the concentration of hydrogen ($H_2$) in another gas such as oxygen ($O_2$), nitrogen ($N_2$), argon (Ar), carbon dioxide ($CO_2$) or even air (assuming that it is of fixed composition), since hydrogen differs greatly from other gases because of its high thermal conductivity in comparison to that of heavier molecules. The following values are given for information purposes:

$$\lambda_{hydrogen} = 0.84 \, Wm^{-1} \, K^{-1}$$

$$\lambda_{air} = 0.012 \, Wm^{-1} \, K^{-1}.$$

Thermal gas sensors generally have an electrically insulating membrane of low thermal inertia, on which devices for heating the membrane and devices for measuring its temperature are arranged. The membrane is conventionally formed from a thin layer of silicon oxide or nitride deposited onto a silicon substrate, which is locally etched to the rear face of the membrane such that a gas flux can circulate on either side thereof. The heating devices and devices for measuring the temperature respectively comprise a first and a second electrical resistance formed by metal lines meandering over the front face of the membrane. The metal used for the temperature measuring devices has a variable resistance as a function of the temperature, such that measuring the voltage at its terminals enables the temperature of the membrane to be determined. When this latter is heated by the heating devices, its temperature rests at a stable value that is dependent on the thermal conductivity of the gaseous mixture or the ambient gas. As a result of this, the measurement of the temperature of the membrane provides an indication of the nature of the ambient gas or of the composition of the gaseous mixture. Reference is made to DE4228484 for more details on the structure and operation of such a gas sensor.

A gas sensor of the type described above allows measurement of a variable of a two-component gaseous mixture, i.e. the concentration of one of the gases, on the basis of one parameter: the temperature of a membrane in physical contact with said mixture. It assists in particular in determining the concentration of hydrogen in another gas, as explained above. There is considerable interest in determining the proportion of hydrogen in another gas with precision, since what is at stake in this case concerns the level of safety of installations and personnel. In fact, it is known that hydrogen forms a highly explosive mixture with oxygen, even at low concentrations. The same applies with air, which contains approximately twenty per cent oxygen. A thermal gas sensor provides such an indication at low cost and space requirement, hence its significant technical interest.

However, the measurement of a variable of a two-component gaseous mixture, in the case in point the concentration of one of the gases, on the basis of one parameter: the temperature of a membrane of low thermal inertia, is only possible if all the other variables of the mixture are constant. In particular, the pressure of the gaseous mixture has a significant influence on its conductivity. At variable pressure, it becomes impossible to determine the concentration of a gas in a two-component mixture on the basis of a single temperature measurement of the membrane.

Such a situation is encountered, for example, within an electrolyser unit. These devices are intended in particular for the production of gaseous hydrogen from water. These are currently the subject of significant developments since they offer a clean energy alternative to fossil fuels. Application EP 2 048 759, for example, describes a domestic installation for the production and storage of gaseous hydrogen using an electrolyser supplied with power by a photovoltaic installation. The hydrogen is then used as fuel in a fuel cell fitted, for example, in an electric vehicle.

In an electrolyser of the type described in application EP 2 048 759 hydrogen is produced from liquid water by means of an anode and a cathode. In a variant, the electrolyser is formed by an assembly of electrolytic cells, each of which having an anode and a cathode. Such a device is described in the patent document GB 1,145,751. Whatever the structure of the electrolyser, hydrogen is produced on the cathode side, while oxygen is produced on the anode side. The accumulation of these gases during the production process, respectively on the cathode side and anode side, causes the pressure within the electrolyser to increase progressively up to a value in the order of ten to several tens of bars. Because of the risks of explosion of an oxygen-hydrogen mixture, it is necessary to detect any presence of hydrogen in the oxygen and vice versa over the entire operating pressure range of the electrolyser. To achieve this and because of the above-mentioned limitation of thermal gas sensors, a pressure sensor is generally added to the gas sensor installed in the electrolyser. It is then possible to combine pressure and temperature measurements to get up to the concentration of gas to be determined. However, this solution increases the cost of this type of detection significantly, which represents a major disadvantage for a domestic installation.

The aim of the present invention is to remedy this disadvantage by proposing a thermal gas sensor that is able to determine the concentration of a gas in a two-component mixture at variable pressure. More specifically, the present invention relates to a sensor for determining the concentration of a gas in a two-component mixture at variable pressure as disclosed and claimed herein.

Because of its features and in particular, as described, the choice of frequency f of the current source supplying the heating devices, the gas sensor according to the invention allows measurement not of one single parameter of the gaseous mixture, i.e. a stable temperature in continuous mode, but two parameters of the gaseous system, one associated with its statics and the other associated with its dynamics. These two parameters inserted into a mathematical function established for this purpose allow determination of not one variable of the gaseous mixture, but two, e.g. the concentration of one of the gases and the pressure of the mixture. Measurement of the pressure of the gaseous mixture by an independent device attached to the gas sensor becomes superfluous.

The present invention also relates to a method for determining the concentration of a gas in a two-component mixture at variable pressure by means of a gas sensor comprising a step of measuring a first characteristic parameter of the conduction of the two-component mixture, a step of measuring a second characteristic parameter of the diffusivity of the two-component mixture and a step of calculating a value of the concentration of said gas and the pressure of said two-component mixture from said parameters with the assistance of a previously established mathematical function and characteristic coefficients of the sensor.

Figure 2:
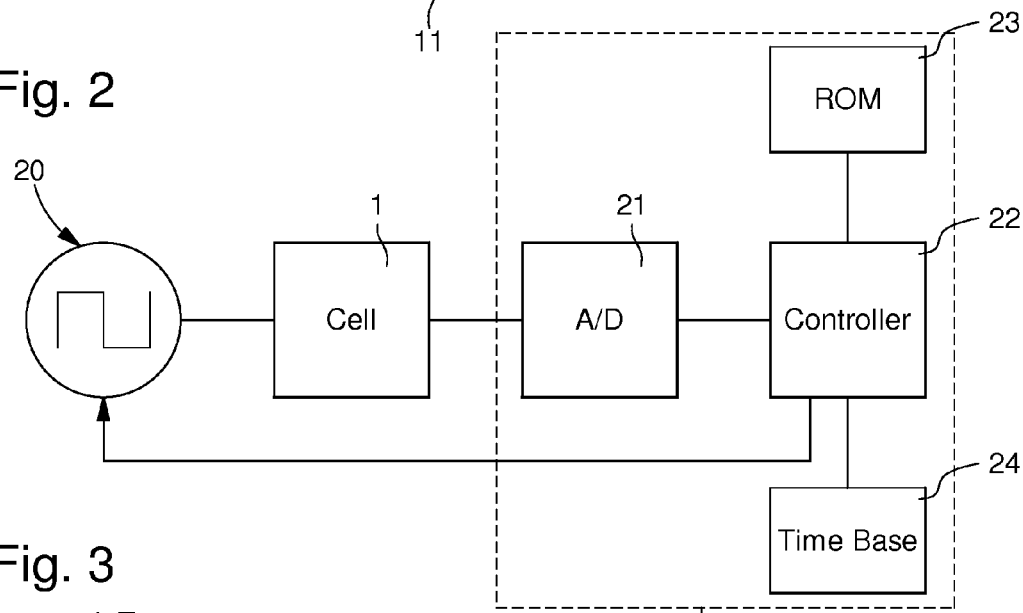
Figure 3:
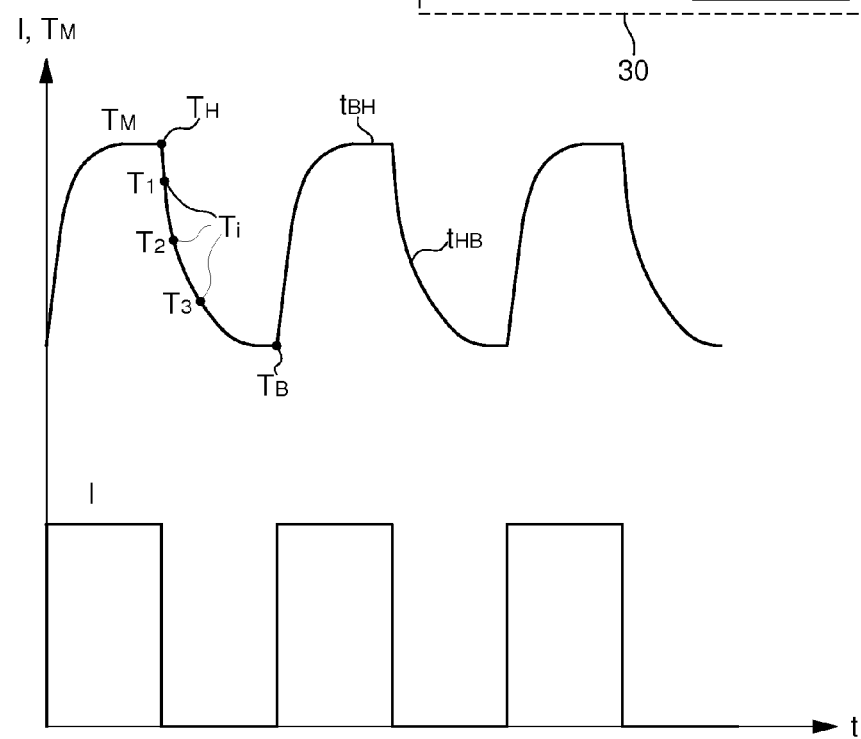

Other features and advantages of the present invention will become evident upon reading the following description provided solely by way of example with reference to the attached drawings:

FIG. 1 is a sectional view of the measurement cell of a gas sensor according to the invention; and FIG. 2 shows a basic operational diagram of the sensor according to the invention; and FIG. 3 shows an example of a measurement signal of said sensor.

As an initial observation, it is mentioned that the gas sensor according to the invention is intended in particular to measure hydrogen in oxygen for the reasons outlined above. However, its operating principle for determining variables of a gaseous mixture can be extended to any two-component mixture. Furthermore one of the two gases can be air, assuming that its composition is constant. In the following description it will be noted that % H and % O are respectively the proportions of hydrogen and oxygen forming the two-component mixture to be analysed and P is its pressure, and there will be no further reference to another gas.

The thermal gas sensor according to the invention conventionally comprises a measurement cell intended to be immersed into two-component oxygen/hydrogen mixture to be analysed, shown schematically in FIG. 1 and given the overall reference 1. The cell 1 comprises a rigid base 10 that has an opening 11 in its centre and is covered by an electrically and thermally insulating membrane 12 of low thermal inertia. The opening 11 allows an ambient gas to circulate and transport heat on either side of the membrane 12. The effect of the conductivity of the gas on the temperature of the membrane 12 thus outweighs the cooling associated with other physical phenomena such as heat radiation or conduction through the base 10. Heating devices 13 are arranged on the membrane 12 at the level of the opening 11, while measuring devices 14 for the temperature $T_M$ of the membrane 12 are situated in the vicinity of the heating devices 13. Measuring devices 15 for the ambient temperature $T_A$ are arranged spaced from the heating devices 13 so as not to be subjected to their effect.

In a particularly advantageous embodiment the cell 1 is made from a sheet of silicon forming the rigid base 10 using production techniques for micromechanical devices well known to the person skilled in the art. The membrane 12 is formed from a layer of silicon nitride $Si_3N_4$ or silicon oxide $SiO_2$ deposited on the sheet of silicon or obtained by thermal nitridation or oxidation. Its thickness is typically several hundreds of nanometers. The opening 11 is generally formed by chemical etching of the silicon sheet from its rear face after formation of the membrane 12. The heating devices 13 as well as the measuring devices 14 for the temperature $T_M$ of the membrane 12 are formed by metal lines meandering over the membrane 12 above the opening 11. The metal used to form the measuring devices 14 has a resistance $R_M$ that varies as a function of temperature in the known manner at a standard reference pressure. The relation linking the resistance $R_M$ to the temperature $T_M$ of the membrane 12 that is well known to the person skilled to the art has the following form:

$$R_M = R_0 * (1 + \alpha T_M) \quad (1)$$

in which the coefficient $\alpha$ is a characteristic of the metal forming the metal line 14: generally platinum, nickel or an alloy of these two metals. In the same way, the measuring devices 15 for the ambient temperature $T_A$ are formed from lines of metal, the resistance $R_A$ of which is thermo-variable. In a similar manner, the ambient temperature $T_A$ is associated with the value of the resistance $R_A$ by relation (1). A passivation layer 16 formed from a silicon oxide $SiO_2$ or a silicon nitride $Si_3N_4$ covers the metal lines 14 and 15.

The cell 1 is powered by an alternating current source 20 shown schematically in FIG. 2 that supplies a square alternating current of frequency f to the heating devices 13. The frequency f lies in the range of between a few hertz and some tens of hertz, depending on the layout and size of the cell 1. Typically, it lies in the order of 20 hertz. It is selected to allow the heating devices 13 to heat and alternately cool the membrane 12 so that its temperature $T_M$ passes from a first stable value $T_H$ to a second stable value $T_B$ and vice versa via transient modes. This aspect of the gas sensor according to the invention will become clearer by looking at FIG. 3. The temperature $T_M$ of the membrane 12 is given by the measuring devices 14, which supply an analog signal representative of $T_M$, for instance a value of the resistance $R_M$ of the metal line forming the measuring devices 14. Moreover, the ambient temperature $T_A$ is given by the measuring devices 15, which supply an analog signal representative of $T_A$, for instance a value of the resistance $R_A$ of the metal line forming the measuring devices 15. It must be noted here that the temperature $T_M$ is a function of the ambient temperature $T_A$ and of the thermal conductivity $\lambda$ of the ambient gas, which is itself a function of the ambient temperature $T_A$ and of the nature of said gas.

$$T_M = f(T_A, \text{conductivity}(T_A, \text{gas})) \quad (2)$$

Consequently, the temperature $T_A$ of the membrane 12 must firstly be corrected in the first order of the effect of the ambient temperature $T_A$ in order to give information about the conductivity of the ambient gas. For this purpose, it is the ratio $R_M/R_A$ that is output from the cell 1, then processed by an electronic circuit 30 comprising a analog to digital converter 21, a controller 22, a memory module 23 and a time base 24.

The analog to digital converter 21 arranged at the output of the cell 1 transforms the analog signal $R_M/R_A$ into a digital signal, which is processed by the controller 22. The ROM memory module 23 (read only memory) connected to the controller 22 stores a plurality of coefficients characteristic of the gas sensor necessary for processing the $R_M/R_A$ signal. These coefficients will be explained below. The controller 22 is also connected to a time base 24 formed by a crystal and to the alternating current source 20, whose frequency fit controls.

We will now refer to FIG. 3 that shows the development of the temperature $T_M$ of the membrane 12, as measured by the resistance $R_M$, and that of the supply current 1 for the heating devices 13 as a function of time. When it is heated by the heating devices 13 in the presence of a gaseous mixture of oxygen and hydrogen, the membrane 12 experiences a rise of its temperature $T_M$ to a high stable value $T_H$ measured by the measuring devices 14. The high value $T_H$ is dependent on the thermal conductivity of the surrounding gaseous mixture that transports the heat supplied by the heating devices 13 reasonably easily. When the heating devices 13 cease to heat the membrane 12, this cools to a low stable value $T_B$ that is substantially equal to the temperature of the ambient medium. Between the high $T_H$ and low $T_B$ stable values, the temperature $T_M$ of the membrane 12 passes through transient modes $t_{HB}$ and $t_{BH}$ of cooling and reheating respectively, which are principally determined by the thermal diffusivity of the surrounding gaseous mixture.

In contrast to thermal conductivity, which defines the behaviour of a gas in static mode, diffusivity characterises the capacity of the gas to progress from one temperature to another and determines its behaviour in dynamic mode. Like thermal conductivity, the diffusivity of the gaseous mix depends on the nature of the gases, their concentration and the ambient pressure, but in a very different manner. According to the invention, the pieces of information supplied by high stable temperature $T_H$ and by the transient cooling mode $t_{HB}$ are combined to determine the composition of the gaseous mixture, whatever its pressure.

In fact, numerous systematic measurements and tests conducted within the framework of the present invention have made it possible to show that the different variables of the gas to be analysed: % H, % O or P, are associated with the value $T_H$ and to the cooling gradient $pt_{HB}$ measured during the transient cooling mode $t_{HB}$ by simple mathematical functions, in which the above-mentioned coefficients play a part. It must be noted here that the cooling of the membrane 12 follows an exponential $e^{-k/T}$ law. The cooling $t_{HB}$ gradient $pt_{HB}$ is thus defined by the following function:

$$pt_{HB}=d/dt(ln((T_H-T_B)/(T_i-T_B))) \quad (3)$$

in which the points $T_i$, three in number, are measured at different intervals during the transient cooling mode $t_{HB}$, for example, at 10, 14 and 18 ms of the point $T_H$ in the present case. It will be noted that the choice of the number of points $T_i$ and of the time interval separating them depends on the layout of the cell 1 as well as numerous other parameters such as the nature of the gases forming the two-component mixture. Consequently, it does not follow a strict rule, but must be conducted empirically in order to take the gradient $pt_{HB}$ into consideration in the best way possible.

Once the calculation of the gradient $pt_{HB}$ has been conducted by the controller 22, the different variables of the oxygen/hydrogen gaseous mixture are provided by mathematical functions to be adapted as a function of the working conditions of the sensor according to the invention. These functions are quite complex, depending on whether the gas to be measured is hydrogen in oxygen or vice versa, or depending on the range of pressure of the gaseous mixture. In fact, hydrogen has a much higher thermal conductivity than oxygen. As a result of this, the high stable temperature $T_H$ is lower in the case of a gaseous mixture formed substantially of hydrogen than in the case of a gaseous mixture formed mainly of oxygen. The difference between $T_H$ and $T_B$ is therefore smaller and the accuracy of the measurement is therefore lower. On the other hand, a broad working pressure range causes greater variations in behaviour of the gaseous mixture than a low pressure range, and this must be taken into account in the calculation of the variables of the gaseous mixture.

In the following description, two mathematical functions are proposed that allow determination of the composition of the gaseous mixture respectively in a simple case and in a more complex case in point. The first case corresponds, for example, to a pressure range of 1 to 5 bar. The second case in point applies, for example, to the detection of a low quantity of oxygen in hydrogen over a pressure range of 1 to 20 bar. It is to be understood that not all the working conditions of the gas sensor according to the invention will be explained in full detail in this description, but the mathematical functions given below can be adapted and modified to correspond to multiple conditions of use of the gas sensor without departing from the framework of the invention.

A first example of working condition relates to the measurement of a concentration of hydrogen ranging from 0 to 2 percent in oxygen over a pressure range varying from 0 to 5 bar. It has been determined by different calculations and tests that the pressure P and the proportion of hydrogen % H can be precisely represented by the following respective functions:

$$P=a*T_H+b*T_H^2+c*pt_{HB}+d*pt_{HB}^2+e*(T_H/pt_{HB})+f \quad (4)$$

$$\%H=A*T_H+B*T_H^2+C*pt_{HB}+D*pt_{HB}^2+E*(T_H/pt_{HB})+F \quad (5)$$

in which coefficients a, b, c, d, e, f and A, B, C, D, E, F are characteristic of the gas sensor and are determined by a calibration procedure. Said calibration consists of measuring values $T_H$ and $pt_{HB}$ for three different pressure ranges and two different concentrations of hydrogen in the ranges of pressure and working hydrogen concentration, then by means of a solver minimising the differences between the measured and calculated values of P and % H. Equations (4) and (5) thus respectively deliver a hydrogen percentage value with an accuracy of 500 ppm and a pressure value with an accuracy of 0.2 bar.

A second example of working condition relates to the measurement of a concentration of oxygen ranging from 0 to 1 percent in hydrogen over a pressure range varying from 0 to 20 bar. In this case, the pressure P and the proportion of oxygen % O can be precisely represented by the following respective functions:

$$P=g*T_H+h*T_H^2+i*pt_{HB}+j*pt_{HB}^2+k*(T_H/pt_{HB})+l \quad (6)$$

$$\%O=G*T_H+H*pt_{HB}+I*pt_{HB}^2+J*(T_H/pt_{HB})+K*(T_A-T_{ref})*(P-P_{ref})+L*(T_A-T_{ref})*(P-P_{ref})+M \quad (7)$$

in which coefficients g, h, i, j, k, l and G, H, I, J, K, L, M are determined as above, $T_A$ is the ambient temperature measured by the measuring devices 15, $T_{ref}$ is the reference temperature at which the calibration points are conducted and $P_{ref}$ is the reference pressure at which the variation of resistance $R_M$ is measured as a function of the temperature. This approach allows the effects of the ambient temperature $T_A$ to be taken into account on the dependence curves of the conductivity of the gas as a function of pressure. This is second-order correction of the temperature. It also takes into account the effects of pressure on the temperature dependence of the measurement resistances 14 and 15. The thus improved equation (7) delivers a value of the proportion of hydrogen with an accuracy of 600 ppm over the entire range of working pressure and the pressure is given by equation (6) with an accuracy of 0.5 bar.

A thermal gas sensor for determining a concentration of gas in a two-component mixture at variable pressure has thus been described. It is understood that the gas sensor according to the invention is not restricted to the embodiments that have just been described and various simple modifications and variants can be envisaged by the person skilled in the art without departing from the framework of the invention as defined in the attached claims.

In particular, the parameters used by the gas sensor according to the invention are the high stable temperature $T_H$ and the cooling gradient $pt_{HB}$. In a particular context, a person skilled in the art could have cause to choose other parameters such as the high stable temperature $T_H$ and the gradient for reheating the membrane $pt_{BH}$ without involving inventive activity. The mathematical functions delivering the variables of the system from measured parameters would thus be potentially significantly different from the functions explained above.

It must also be mentioned that other means for heating the membrane 12 or for measuring its temperature are part of the framework of the present invention. For example, it is known that the temperature of a membrane immersed in a gas to be analysed can be delivered by a diode rather than by a metal line with thermo-variable resistance. Moreover, it is conceivable that another element of low thermal inertia such as a filament can be used in place of a membrane.

Finally, it is noted that the present invention relates to a method for determining the concentration of a gas in a two-component mixture at variable pressure. Said method is based on the measurement of a parameter in stable mode and a parameter in transient mode of the gaseous mixture and on the determination of a mathematical function to calculate the variables of the gaseous mixture from these parameters. A gas sensor has been described above that is particularly well suited to measuring these values and for application of this method. However, the method according to the invention is not restricted to such a sensor, but can be extended to any sensor that delivers the above-mentioned measurements by any appropriate means.

What is claimed is:

1. A sensor for determining the concentration of a gas in a two-component mixture at variable pressure, comprising:
    a measurement cell located in the two-component mixture, comprising a membrane of low thermal inertia, on which heating means for said membrane and measuring means that supplies a signal representative of the temperature $T_M$ of said membrane are arranged side by side,
    a source of alternating current of a predetermined frequency f for supplying said heating means and
    an electronic circuit,
    wherein said predetermined frequency f enables the heating means to heat and alternately allow said membrane to be cooled so that its temperature $T_M$ passes from a first stable value to a second stable value and vice versa via a transient mode, said first and second stable values being respectively a high stable temperature $T_H$ of said membrane and a low stable temperature $T_B$, and said transient mode being a transient cooling mode $t_{HB}$ of said membrane, and
    wherein the electronic circuit processes said signal to extract therefrom a first and a second parameter respectively relating to said first stable value and to the transient mode, and calculates a value of the concentration of said gas and of the pressure of said two-component mixture from these parameters with the assistance of a previously established mathematical function and characteristic coefficients of said sensor, said first parameter being representative of said high stable temperature $T_H$ and said second parameter being representative of the rate of cooling of said membrane $pt_{HB}$ during said transient cooling mode.

2. The sensor according to claim 1, wherein the cooling rate of the membrane $pt_{HB}$ is given by the following function:

$$pt_{HB} = d/dt(ln((T_H - T_B)/(T_i - T_B)))$$

in which the points $T_i$ are chosen at different intervals during the transient cooling mode $t_{HB}$ of said membrane.

3. The sensor according to claim 2, wherein the concentration of a gas of said two-component mixture is a polynomial function of said parameters representative of the high stable temperature $T_H$ and the cooling rate $pt_{HB}$ of the following type:

$$A*T_H + B*T_H^2 + C*pt_{HB} + D*pt_{HB}^2 + E*(T_H/pt_{HB}) + F$$

in which A, B, C, D, E and F are included in said characteristic coefficients of the sensor and are obtained by calibration of said sensor.

4. The sensor according to claim 2, wherein the pressure of said two-component mixture is a polynomial function of said parameters representative of the high stable temperature $T_H$ and the cooling rate $pt_{HB}$ of the following type:

$$a*T_H + b*T_H^2 + c*pt_{HB} + d*pt_{HB}^2 + e*(T_H/pt_{HB}) + f$$

in which a, b, c, d, e and f are included in said characteristic coefficients of the sensor and are obtained by calibration of said sensor.

5. The sensor according to claim 2, wherein the concentration of a gas of said two-component mixture is a polynomial function of said parameters representative of the high stable temperature $T_H$, of the cooling rate $pt_{HB}$, of the ambient temperature $T_A$, of a reference temperature $T_{ref}$ and of a reference pressure $P_{ref}$ of the following type:

$$G*T_H + H*pt_{HB} + I*pt_{HB}^2 + J*(T_H/pt_{HB}) + K*(T_A - T_{ref})*(P - P_{ref}) + L*(T_A - T_{ref})*(P - P_{ref}) + M$$

in which G, H, I, J, K, L and M are included in said characteristic coefficients of the sensor and are obtained by calibration of said sensor, and in which $T_{ref}$ is the reference temperature at which the calibration is conducted and $P_{ref}$ is the reference pressure at which said signal is calibrated as a function of the temperature of the membrane.

6. The sensor according to claim 1, wherein the sensor additionally comprises measuring devices that supply a signal representative of the ambient temperature $T_A$ of the gaseous mixture, and wherein said signal representative of the temperature of the membrane is firstly corrected from the signal representative of the ambient temperature.

* * * * *